United States Patent
Khan et al.

(10) Patent No.: US 10,845,195 B2
(45) Date of Patent: Nov. 24, 2020

(54) SYSTEM AND METHOD FOR MOTION BASED ALIGNMENT OF BODY PARTS

(71) Applicant: SolitonReach, Inc., Columbus, OH (US)

(72) Inventors: Furrukh Khan, Dublin, OH (US); Xiaoxi Zhao, Columbus, OH (US)

(73) Assignee: SolitonReach, Inc., Columbus, OH (US)

( * ) Notice: Subject to any disclaimer, the term of this patent is extended or adjusted under 35 U.S.C. 154(b) by 0 days.

(21) Appl. No.: 16/713,974

(22) Filed: Dec. 13, 2019

(65) Prior Publication Data

US 2020/0116488 A1    Apr. 16, 2020

Related U.S. Application Data

(63) Continuation-in-part of application No. 15/200,880, filed on Jul. 1, 2016, now Pat. No. 10,698,501.

(60) Provisional application No. 62/779,047, filed on Dec. 13, 2018, provisional application No. 62/221,170, filed on Sep. 21, 2015, provisional application No. 62/187,426, filed on Jul. 1, 2015.

(51) Int. Cl.
*G01C 19/5776* (2012.01)

(52) U.S. Cl.
CPC .............................. *G01C 19/5776* (2013.01)

(58) Field of Classification Search
None
See application file for complete search history.

(56) References Cited

U.S. PATENT DOCUMENTS

| | | | |
|---|---|---|---|
| 9,068,843 B1 | 6/2015 | Sohn | |
| 9,785,247 B1 | 10/2017 | Horowitz | |
| 9,838,846 B1* | 12/2017 | Le Grand | G01C 21/165 |
| 2005/0253806 A1 | 11/2005 | Liberty | |
| 2007/0213889 A1* | 9/2007 | Parra Carque | G05D 1/101 |
| | | | 701/7 |
| 2009/0070566 A1 | 3/2009 | Schreiner | |
| 2009/0138746 A1 | 5/2009 | Klemer | |
| 2011/0254760 A1 | 10/2011 | Lloyd | |
| 2013/0222565 A1 | 8/2013 | Guerin | |

(Continued)

OTHER PUBLICATIONS

Madgwick, S.O.H., et al., "Estimation of imu and marg orientation using a gradient descent algorithm, in: 2011 IEEE International Conference on Rehabilitation Robotics", 2011, (pp. 1-7), doi: 10.1109/ICORR.2011.5975346; https://www.x-io.co.uk/res/doc/madgwick_internal_report.pdf, (7 pgs.).

(Continued)

*Primary Examiner* — Stephen T. Reed
(74) *Attorney, Agent, or Firm* — Benesch, Friedlander, Coplan & Aronoff LLP

(57) ABSTRACT

The embodiments described herein relate to systems, methods, and devices for high precision inertial measurement sensing of functional movement and range of motion analysis with close to zero drifts in sensor orientation readings. The system calibrates IMU raw data samples after warm up, and uses a fast convergent fusion algorithm to calculate high accuracy and almost drift free orientation information. In some examples, the systems, methods, and devices are used in computer-guided or robotic surgery, to aid in evaluation before, during, and after a surgical operation.

18 Claims, 13 Drawing Sheets

(56) References Cited

U.S. PATENT DOCUMENTS

| | | |
|---|---|---|
| 2013/0254582 A1 | 9/2013 | Wada |
| 2014/0278217 A1 | 9/2014 | Keal |
| 2015/0177020 A1 | 6/2015 | An |
| 2015/0185002 A1* | 7/2015 | Yang .................. G01C 19/00 702/151 |
| 2015/0220109 A1 | 8/2015 | von Badinski |
| 2015/0288687 A1 | 10/2015 | Heshmati |
| 2016/0091955 A1 | 3/2016 | Black |
| 2016/0327396 A1 | 11/2016 | Hallberg |
| 2016/0363460 A1 | 12/2016 | Sarbishei |
| 2016/0378265 A1 | 12/2016 | Katsurahira |
| 2017/0273665 A1 | 9/2017 | Kapoor et al. |
| 2017/0357332 A1* | 12/2017 | Balan .................. G02B 27/0093 |
| 2017/0363423 A1* | 12/2017 | Dormody ............... G01C 17/38 |

OTHER PUBLICATIONS

Wilson, S., et al., "Formulation of a new gradient descent MARG orientation algorithm: Case study on robot teleoperation, Mechanical Systems and Signal Processing", vol. 130, 2019, (pp. 183-200) ISSN 0888-3270; https://doi.org/1/1016/j.ymssp.2019.04.064, (18 pgs.).

International Search Report in International Application No. PCT/US2016/040737, dated Nov. 23, 2016, (5 pgs.).

Written Opinion in International Application No. PCT/US2016/040737, dated Nov. 23, 2016, (9 pgs.).

International Search Report and Written Opinion in International Application No. PCT/US19/66303, dated Feb. 24, 2020 (13 pages).

* cited by examiner

SYSTEM AND METHOD FOR MOTION BASED ALIGNMENT OF BODY PARTS

CROSS-REFERENCE TO RELATED APPLICATIONS

This Application claims priority to U.S. Provisional Patent Application Ser. No. 62/779,047, titled "System And Method For Motion Based Alignment Of Body Parts," filed on Dec. 13, 2018. This Application further claims priority to, and is a Continuation-In-Part Application of, U.S. patent application Ser. No. 15/200,880, titled "Systems And Methods For Three Dimensional Control Of Mobile Applications," filed on Jul. 1, 2016, which claims priority to U.S. Provisional Patent Application No. 62/187,426, filed on Jul. 1, 2015, and U.S. Provisional Patent Application No. 62/221,170, filed on Sep. 21, 2015, all of which are incorporated by reference herein in their entireties.

BACKGROUND

Motion capture devices frequently require the use of body suits or harnesses, which can diminish user experience. Moreover, even with the complexity of such motion capture devices, the motion capture devices frequently generate excessive amounts of sensor drift, i.e., the sensor erroneously detects motion when the user is stationary.

Motion capture devices may enable a surgical robot to assist a physician to properly align a cut and fit a prosthesis into a bone. These motion capture systems rely on camera-based optical tracking that is pinned to the bone, increasing a risk of injury during the procedure and requiring camera line of sight. Any disruption or bumping of the marker or occlusion of the line of sight during a measurement can be problematic.

Inertial measurement unit (IMU)-based sensor systems are known to suffer from drift, making them unsuitable for high-precision repeated measurements in computer-guided or robot assisted surgical procedures. In addition, IMU-based sensor systems on the market may require wires to connect to the data collection system or have a short battery life.

BRIEF DESCRIPTION OF THE DRAWINGS

The embodiments set forth in the drawings are illustrative in nature, and are not intended to limit the subject matter defined by the claims. The following detailed description of the illustrative embodiments can be understood when read in conjunction with the following drawings, where like structure is indicated with like reference numerals, and in which:

SUMMARY

Figure 1A:
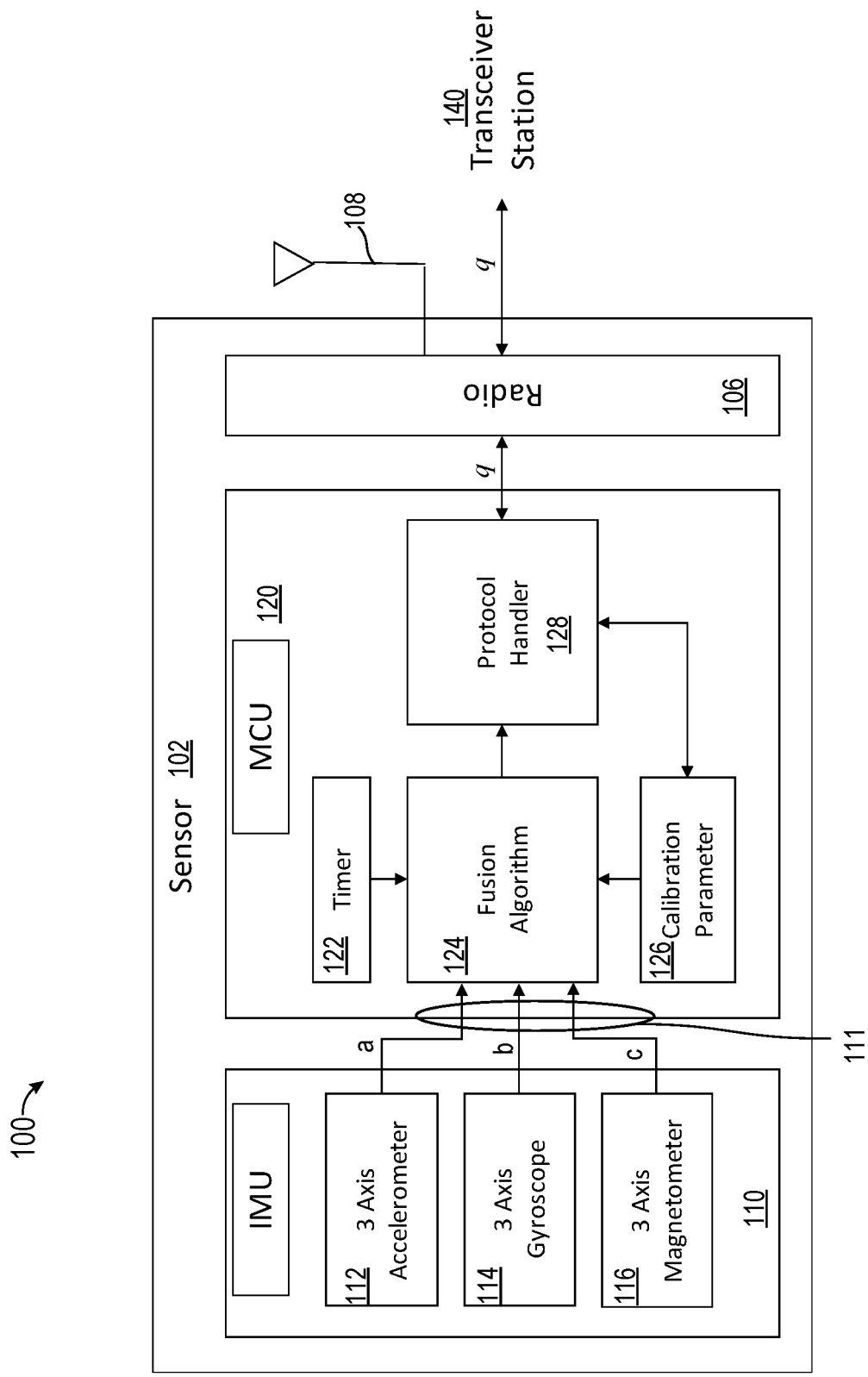
FIG. 1A is a block diagram of an example sensor system.

Systems can provide inertial measurement sensing of functional movement and range of motion analysis. In some examples, the system includes wireless sensors with long battery life and negligible drift, making them suitable for repeatable measurements in clinical and sports applications. In some examples, the sensors can be used for computer-guided surgical applications in total knee, partial knee, and total hip replacements for traditional and/or robotic procedures. Other example implementations can include, but are not limited to, applications in Cerebral Palsy, Muscular Dystrophy, and stroke rehabilitation.

In some examples, the system includes inertial measurement unit (IMU) sensors, e.g., electronic devices that measure and report a body's specific force, angular rate, and/or the magnetic field surrounding the body, using a combination of accelerometers and gyroscopes, and/or magnetometers. An example IMU is described in commonly owned U.S. Patent Publication No. US2017/0024024A1 entitled "Systems and Methods for Three Dimensional Control of Mobile Applications," the description of which is incorporated by reference herein in its entirely. For use in motion capture, a fusion algorithm and IMU sensors can be used to derive the relative movement of limbs, without requiring any cameras to track ongoing motion.

In the field of arthroplasty (knee surgery), the system can be used inside and/or outside the operating room, e.g., before the operation to determine mobility, during the operation to aid with the surgery, and after the operation to aid with physical therapy. For example, arthroplasty involves measurement of angles in three dimensions and reporting of static limb positions. In some examples, the system's sensors can improve robotic knee surgery, by replacing an otherwise cumbersome optical tracking system with an inertial movement based tracking system using the sensors. In some examples, the sensors are single use. For example, to avoid having to clean and sterilize the sensors between procedures and to avoid problems caused by battery charging, the sensors for this application can be disposable components used as part of the surgery and billable as disposable medical equipment (DME).

The sensors can be integrated into a software of a robot, which integrates motion tracking data with patient CT scans and other clinical information so that the robot may move around the patient's knee. The sensors may simplify surgical workflow, reduce risk of injury, and reduce the training costs of adopting robotic surgery. Surgical robots assist the surgeon in making the cut into the bone at a proper angle, reducing variability in results due to human error, and ultimately improving outcomes. The robotic field includes Stryker's Mako robot. In traditional (non-robotic) knee surgery, the field includes products that enable physicians to objectively assess knee joint function before and after the procedure, and for fitting the implant during surgery. The application of the IMU sensors may help reduce malpractice risk, improve patient outcomes, and make traditional knee surgery more competitive with robotic technology at a fraction of the cost.

For the rehabilitation market, the system includes communicating sensor data, which may be used to ensure that patients properly do their exercises at home, and may enable physicians to remotely monitor patient compliance. Poor compliance with exercise regimens can be a significant contributor to sub-optimal outcomes following surgery.

While particular embodiments have been illustrated and described herein, various other changes and modifications may be made without departing from the spirit and scope of the claimed subject matter. Moreover, although various aspects of the claimed subject matter have been described herein, such aspects need not be utilized in combination. The appended claims are intended to cover all such changes and modifications that are within the scope of the claimed subject matter.

DETAILED DESCRIPTION

FIG. 1A is a block diagram of an example sensor system 100. The sensor system 100 includes an IMU 110, a microcontroller unit (MCU) 120, and a transceiver radio 106. The IMU 110 may include a three-axis accelerometer 112, a three-axis gyroscope 114, and a three-axis magnetometer 116. The MCU 120 includes a processor circuit that includes at least an on-chip timer 122, samples data periodically from the IMU 110, reads factory pre-installed calibration parameter 126 from a persistent memory, and executes a fusion algorithm 124 to process orientation data of the sensor 102. A protocol handler 128 formats processed orientation data from the MCU 120 to be transmitted wirelessly by an on-chip radio 106 through an antenna 108. In an example, the IMU 110 may be physically separated from the MCU 120 by a certain distance. In another example, the IMU 110 and the MCU 120 may be integrated within a single package as shown in FIG. 1B.

Figure 1B:
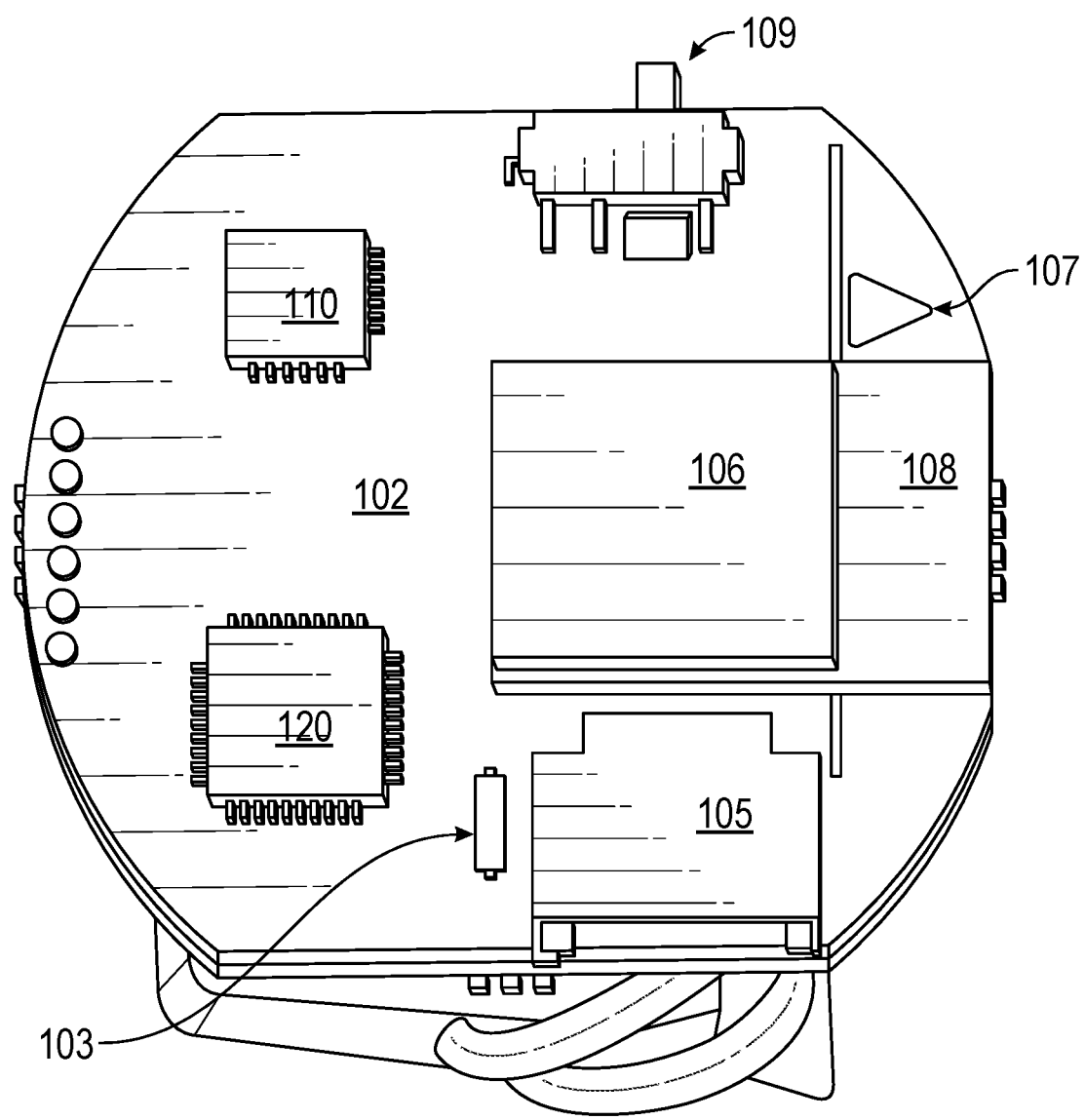
FIG. 1B is an example physical sensor as depicted in FIG. 1A.

FIG. 1B is an example physical sensor as depicted in FIG. 1A. In an example, an actual size of the sensor 102 may be measured with a dimension of no more than 1.1 inch width by 1.1 inch length, and weighing no more than six grams. The sensor 102 is small enough to be attached externally onto a body part, or implanted within a body part in a surgical procedure to monitor alignment of a prosthetic apparatus, or motion trajectory of the body part after an alignment procedure.

The sensor 102 may include an onboard rechargeable or non-rechargeable Li-ion battery 105 having a continuous operating lifetime of no less than seven hours to power the IMU 110, MCU 120, and the onboard radio 106. Floating-point computation is run in a software environment, which is extremely inefficient (slow). To increase battery life, the MCU 120 used in the disclosed sensor 102 is, in one example, so low powered that it does not even have a hardware Floating Point Processor. The big challenge of using such a small MCU is the need to run a demanding fusion algorithm on it. In this example, the challenge may be tacked by implementing the fusion algorithm in fixed point arithmetic, by using Texas Instruments IQmath fixed point arithmetic library. Using this library has an additional advantage that it is more efficient (faster) than performing floating point operations via a hardware Floating Point Processor.

The radio 106 may include a patch antenna 108 on a printed wire board (PWB). As shown in FIG. 1B, an arrow mark 107 may be printed onto the sensor 102 to indicate a reference Y' axis direction within a local frame reference of the IMU 110 having coordinate axes of X', Y', and Z'. The local frame in the IMU 110 forms a right handed X', Y', and Z' coordinate system with respect to a common origin O', and directions of X' and Y' axes are pre-oriented on the IMU as shown by the arrow 107 in FIG. 2. Each sensor may be identified by a unique serial number printed thereon during manufacturing. A mechanical switch 109 may be used to turn on the power of the sensor when used and a light emitting diode (LED) 103 may be used to indicate an on/off power state of the sensor 102.

The IMU 110 and the MCU 120 may operate as a pair. In an example, the IMU 110 may be physically separated from the MCU 120 by a certain distance and connected by physical wires. In another example, the IMU 110 and the MCU 120 may be integrated within a single package as shown in FIG. 1B. In operation, respective IMU raw data a, b, c may be generated in digital format by the three-axis accelerometer 112, a three-axis gyroscope 114, and a three-axis magnetometer 116, respectively, and sent to the MCU 120 to generate corresponding orientation data samples. The MCU 120 may first sample the IMU raw data a, b, c within a periodic time interval $\Delta t$. The sampled raw data a, b, c may afterwards be corrected by the MCU 120 by the IMU 110 specific calibration parameter 126 (factory pre-installed as firmware) read from a persistent memory, to correct the sampled raw data a, b, c to stay within a pre-defined range of accuracy and/or drift variations.

Figure 2:
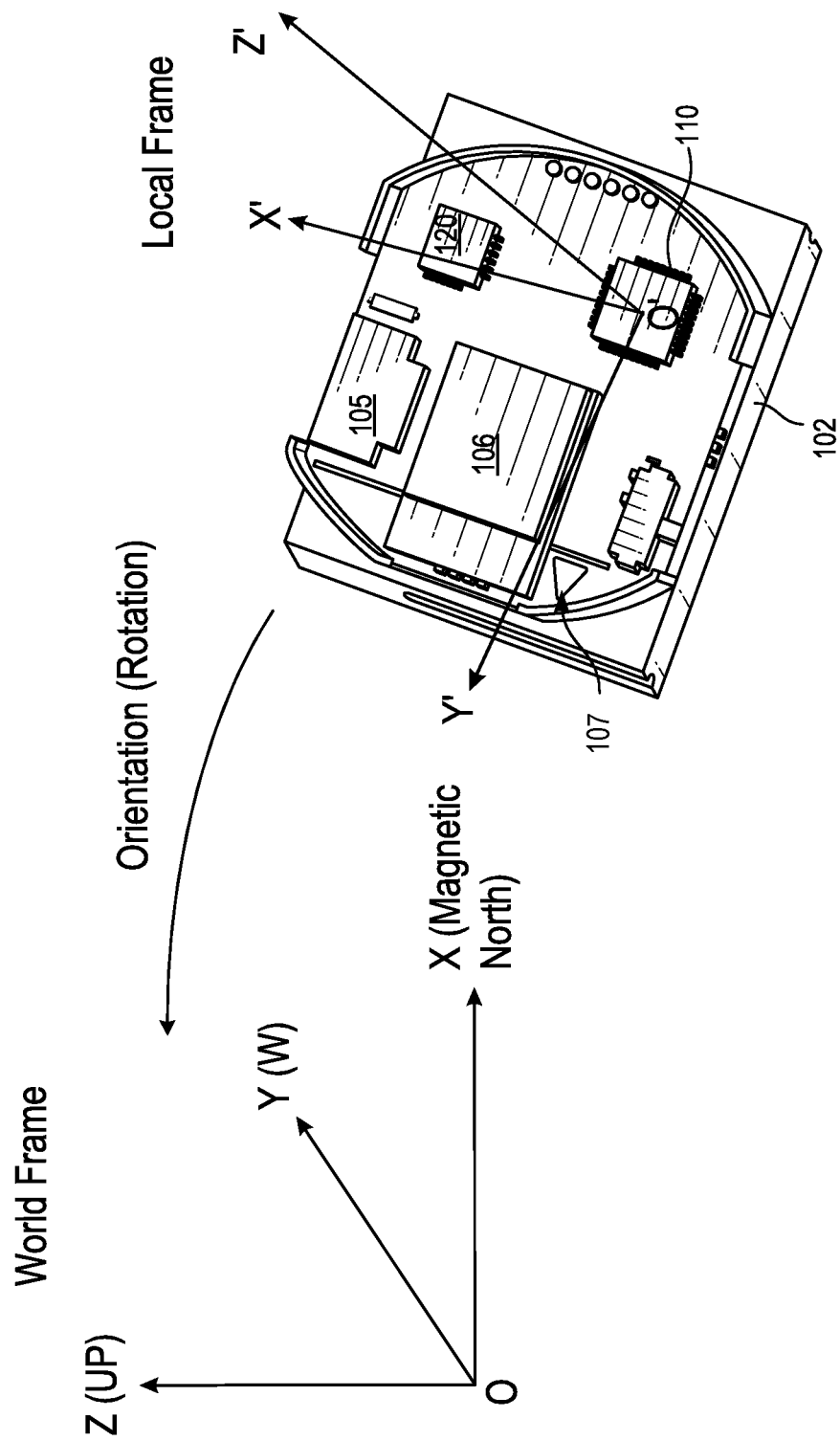
FIG. 2 illustrates an example sensor orientation determination.

After calibration and raw data corrections, the MCU 120 may then execute a fusion algorithm 124 in fixed point computation (versus CPU floating point computation) to transform the corrected sampled raw data a, b, c into corresponding plurality of IMU orientation data samples, through rotating the local frame coordinate axes of X', Y', and Z' of each corrected plurality of IMU data samples a', b', c' by an amount until the local frame of the IMU 110 is aligned with or matched to a world frame (see FIG. 2). The world frame forms a right-handed X, Y, and Z coordinate system with respect to a common origin O, with an x-axis that points in a magnetic North direction, a z-axis that points upward with respect to the earth ground, and a y-axis that is perpendicular to an XZ plane. The transformed corresponding plurality of sensor's orientation data samples q may then be transmitted by the radio 106 to a remote station 140.

Since the alignment of the local frame to the world frame is an orientation rotation, mathematically such orientation may be represented by a rotation matrix. Euler angles may be derived from this matrix. In practice, dealing directly with Euler angles may lead to mathematical singularities related to gimbal lock. Rotations can also be represented by mathematical entities known as quaternions, which do not suffer from gimbal lock singularities. Strictly speaking, quaternions are a four-dimensional generalization of two-dimensional complex numbers. Quaternions may be understood as vectors or arrays having four real elements that can represent rotations (orientation). The MCU 120 in sensor 102 may calculate this orientation (quaternion) periodically (using Madgwick's fusion algorithm modified by a frequency dependent $\beta$) at a sampling rate at 190 Hz and emit this information in wireless packets at a transmission rate such as at 120 Hz through the radio 106 using an antenna ANT protocol without using Blue Tooth Low Energy (BLE) protocol for wireless communication.

Figure 3:
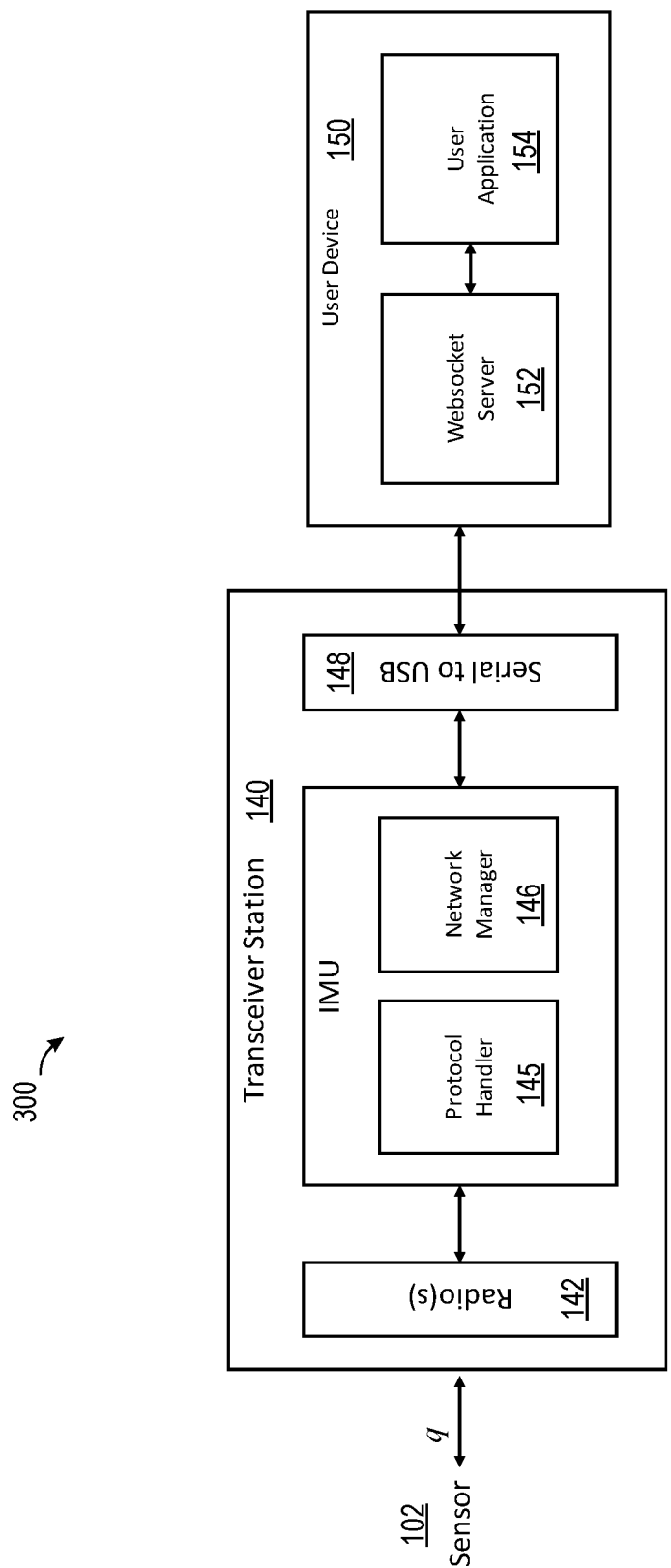
FIG. 3 illustrates a system block diagram to communicate sensor orientation data to remote devices.

FIG. 3 illustrates a system block diagram 300 to communicate sensor orientation data to remote devices. In an implementation, the remote station 140 may be a transceiver station including a radio 142 that receives the sensor's orientation data samples q (in quaternions). The remote station 140 may re-format the sensor's orientation data samples q in a wireless protocol format to a Universal Serial Bus (USB) format industry standard that may readily be powered by a power supply and communicated to another user device 150 such as a computer, or a peripheral device through USB cable connections. The user device 150 may function as a WebSocket server 152 that directly streams messages of the sensor's orientation data samples q on a web browser through a WebSocket protocol. The Websocket Server 152 and User Application 154 need not be located on the same device. For example, the User Application 154 may reside on another device, such as another PC/Mac/desktop or a mobile device (iPad, iPhone, Android phone/tablet) and communicate with the Websocket Server 152 via Websockets.

Figure 4:
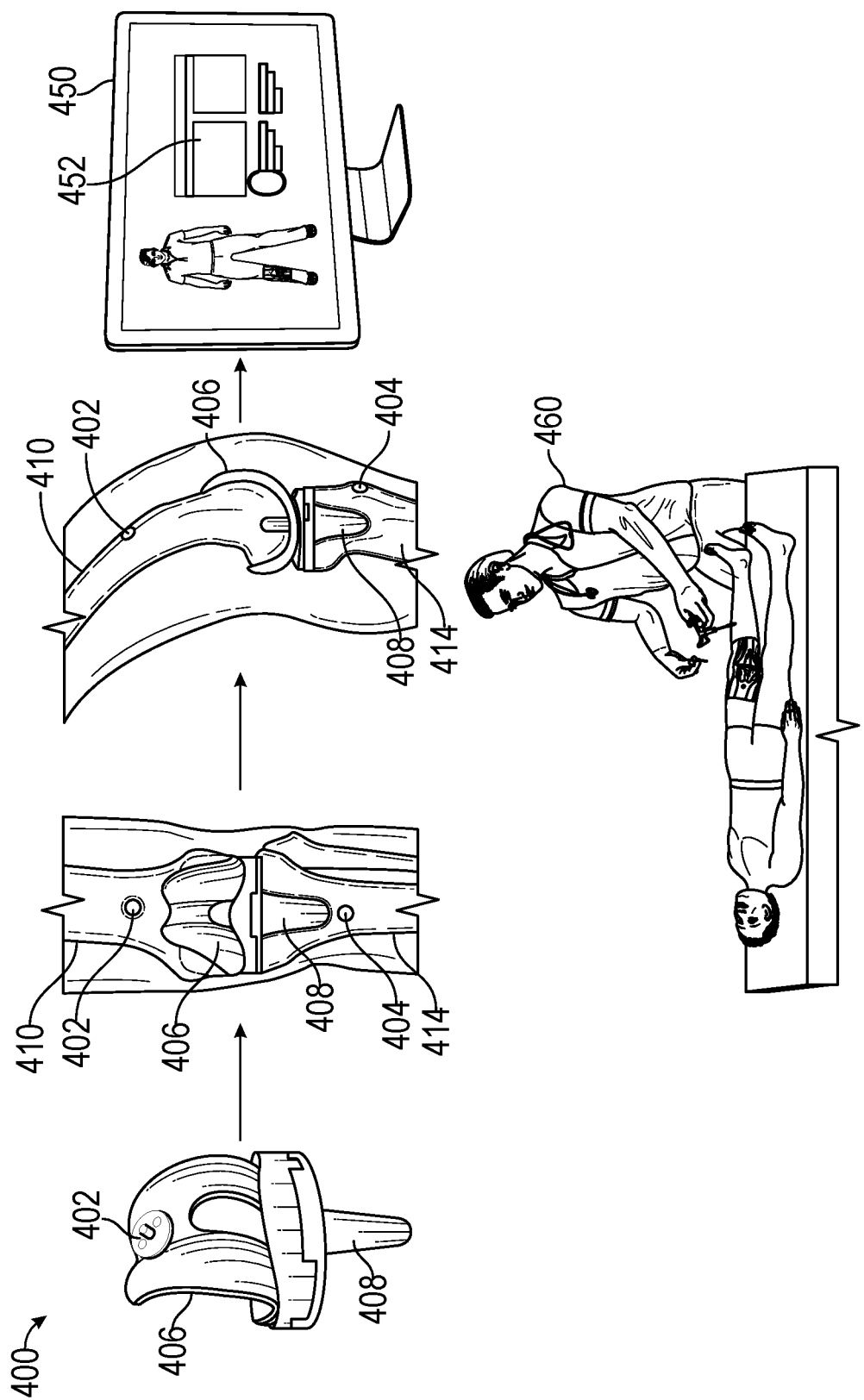
FIG. 4 illustrates an example sensor orientation implementation in computer-guided surgery.

FIG. 4 illustrates an example sensor orientation implementation in computer-guided surgery. In this example, a sensor system 400 may include a plurality of sensors 402, 404. Orientation data sent out by sensors 402, 404 to a monitor 450 may enable a physician 460 to custom fit a knee implant 406 to a femur bone 410, and custom fit a knee plate 408 to a tibia 414 of a patient in the operating room. The orientation data sent out by sensors 402, 404 improves precisions in an alignment and angular movement of the patient's knee during the procedure and after the procedure in the clinic, without using an expensive surgical robot. In other examples, the system 400 may improve on surgical robot surgeries, e.g., by providing small, lightweight, and/or wireless sensors, with long battery life that do not rely on line of sight to operate (e.g., see FIGS. 4-5). The sensors 402, 404 may be attached to the bones 410, 414 and/or implant of the user/patient and/or be wearable by the user/patient. Wireless communication may include sending the orientation data to the monitor 450.

Figure 5:
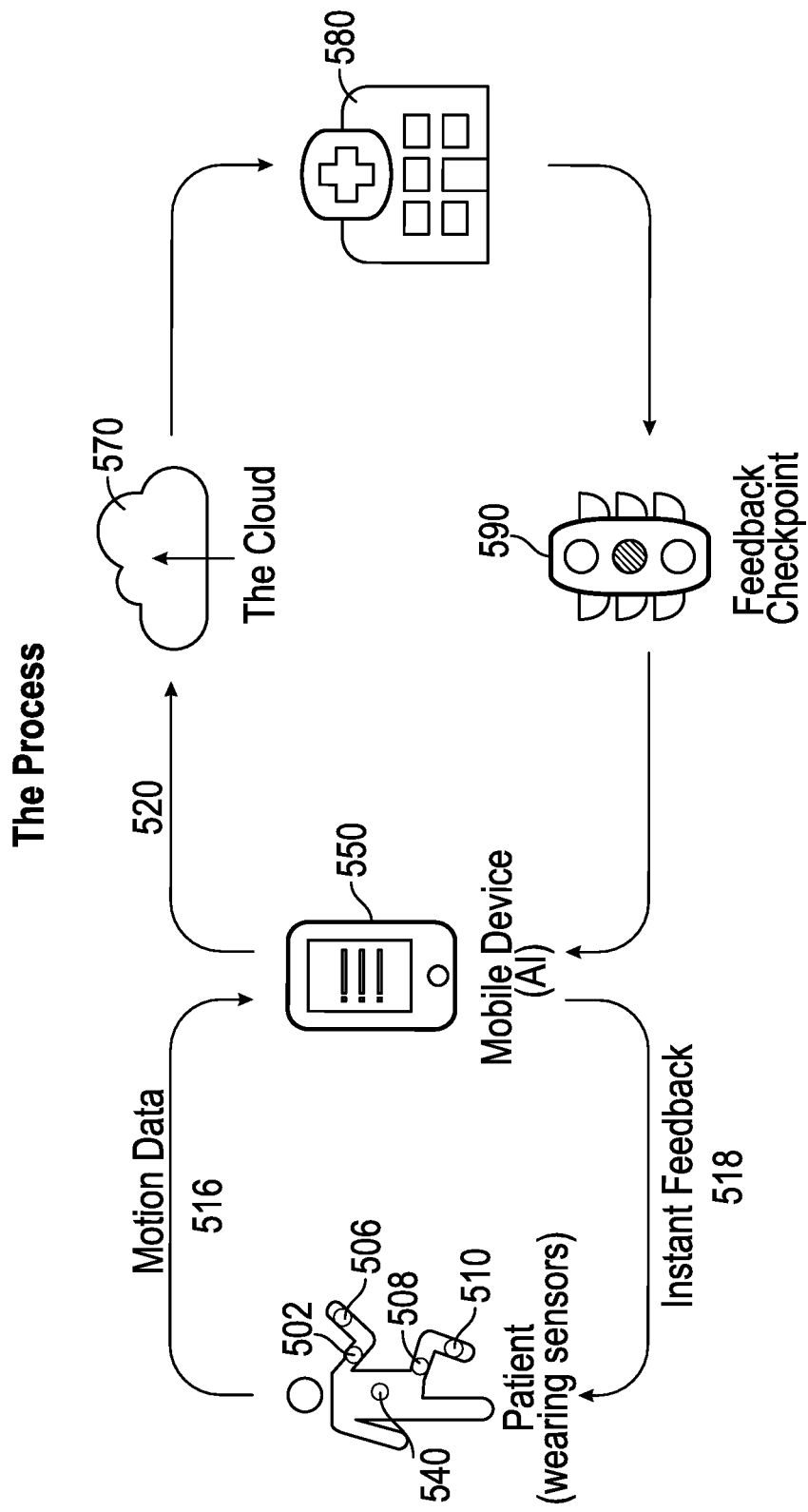
FIG. 5 illustrates an example communication system to communicate sensor orientation data.

FIG. 5 illustrates an example communication system 500 to communicate the sensors' 502-510 motion and/or orientation data. In some examples, orientation and motion information 516 from sensors 502-510 may be wirelessly transmitted to a remote station 540, which may be re-formatted into USB serial data 516 to be re-transmitted to a mobile device 550 of the user/patient for processing and/or storage. The mobile device 550 of the user may utilize a WebSocket protocol to process the received orientation data 516 for viewing on a browser, and may forward the data 520 in Web Socket protocol to remote processing and/or data storage servers, e.g., the cloud 570. In some examples, data from the cloud 570 may be accessed by other entities, e.g., a device of a doctor and/or physical therapist, e.g., via a portal, application, or application programming interface (API). The device 580 of the doctor and/or physical therapist can be used to send additional information to the mobile device 550 of the user/patient, e.g., for viewing by the user/patient 540. The mobile device 550 may send instant visual and/or audio feedback 518 to the user/patient based on the sensors' transmitted orientation data.

In some examples, data 516 from the sensors 502-510 may integrate with electronic medical records systems and with other application-specific software that assists the clinician to customize knee implants. In the rehabilitation application, cloud-based software can be used to remotely monitor patient compliance. A software as a service (SaaS) model, for example, may allow clinics to receive ongoing services and amortize the cost of the hardware over time. As a result, users, doctor, and physical therapists are insulated from the intricacies of serial communications and managing raw data packets originating from the remote station 540.

Better outcomes can lead to happier patients, increased word of mouth referrals, fewer revisions, and less drain on the health care dollars. Having objective numbers can also allow for concrete conversations with patients. It also gives patients data on the point they started, what they are improved to, and numbers to achieve for a full recovery. Accurate information may also allow research data to be repeatable and comparable.

In another example, the sensors 502-510 wirelessly transmit orientation data in the form of quaternions to a remote station 540. The remote station 540 may be plugged into a desktop as a server via USB communication.

Referring to the IMU 110 used in the sensor 102, it may be a low-cost MEMS (Micro Electrical Mechanical System) 9-axis IMU, made up of a 3-axis magnetometer 116 that measures the X', Y', and Z' coordinates according to a magnetic field's direction vector (North pole) of the IMU in the local frame, a 3-axis accelerometer 112 that measures the X', Y', and Z' coordinates according to an acceleration of the IMU in the local frame, and a 3-axis gyroscope 114 that measures the X', Y', and Z' coordinates of an angular velocity of the IMU in the local frame. Note that the 9-axis IMU is sometimes also known as a MAG (Magnetic, Angular Rate and Gravity) sensor.

Regarding the 3-axis magnetometer 116, in an absence of any magnetic or ferromagnetic materials in its environment, the 3-axis magnetometer 116 would measure the three components (in X', Y', and Z' in local frame) of the Earth's magnetic field's vector. It is worth noting that this vector is not parallel to the ground. Rather, it has an inclination (for example, ~64° in Columbus, Ohio) with respect to the ground having the X axis pointing to the north pole, the Z axis pointing up, and the Y axis pointing out of the page (West direction) with reference to the world frame. In practice, an improved steepest decent method modified from Madgwick's fusion algorithm will be used to immune from the effects of the inclination angle.

In practice, the environment in which the IMU 110 is placed may have magnetic and ferromagnetic materials which will modify the Earth's magnetic field at the location of the IMU 110. Therefore, the measured North pole direction will not coincide with the Earth's North pole direction. This will not pose any problem for the sensors if two conditions are met: (i) the resultant magnetic field is uniform (the strength of the magnetic field has no detrimental effect on the sensors as long as it is uniform), (ii) all the sensors being used together are in the same magnetic environment, and therefore they all see the same magnetic field (i.e. the same World frame).

However, even if the above two conditions (i) and (ii) are met, it may happen that the magnetic field varies with time because of the environment. These causes may be a result of switching of electrical machinery (like motors), people moving around in a vicinity of strong magnets, or large ferromagnets placed very close to the magnetometer 116. Effects like these will produce variations in the measured magnetic field with respect to time. Such variations are known as magnetic noise. It is not a defect in the magnetometer; it is simply noise picked up from the environment. One of the goals of the factory preset IMU specific calibration parameters 126 is to minimize the effect of magnetic noise.

Presence of magnetic and ferromagnetic materials can distort the Earth's magnetic field to become non-uniform which causes erroneous readings on the magnetometer 116. Therefore, magnetic and ferro-magnetic materials should be kept at least two feet away from the magnetometer 116 sensor when in use. Furthermore, there may be distortions caused by metals fixed on the magnetometer 116 sensor which are in close proximity to the IMU 110, like soldering material, and electronic components on the PCB such as the ANT radio 106, MCU 120 and LDO (Low Dropoff Regulator). The attached Li ion battery 105 may also have ferromagnetic components. Thus, the factory calibration parameters 126 may correct the Magnetometer 116 to correct for these distortions.

The accelerometer 112 measures the three components (in X', Y', and Z' in local frame) of the linear acceleration experienced by the IMU 110. The accelerometer may be used to indicate an UP direction, i.e., the Z axis of the world frame. When the accelerometer is at rest (i.e., static to semi-static condition), it only experiences an acceleration due to gravity which points downward, and the calibration parameter 126 to correct an UP direction may be determined by taking a negative of the measured acceleration.

When the accelerometer 112 undergoes dynamic translational changes or rotation then it experiences additional linear and centripetal accelerations on top of the acceleration due to gravity, and the total acceleration measured by the accelerometer no longer points in the downward direction. Thus, under dynamic conditions, the negative of the measured acceleration can give us a false UP direction as shown in the next figure. This error in the UP direction may be termed as accelerometer noise.

Figure 6:
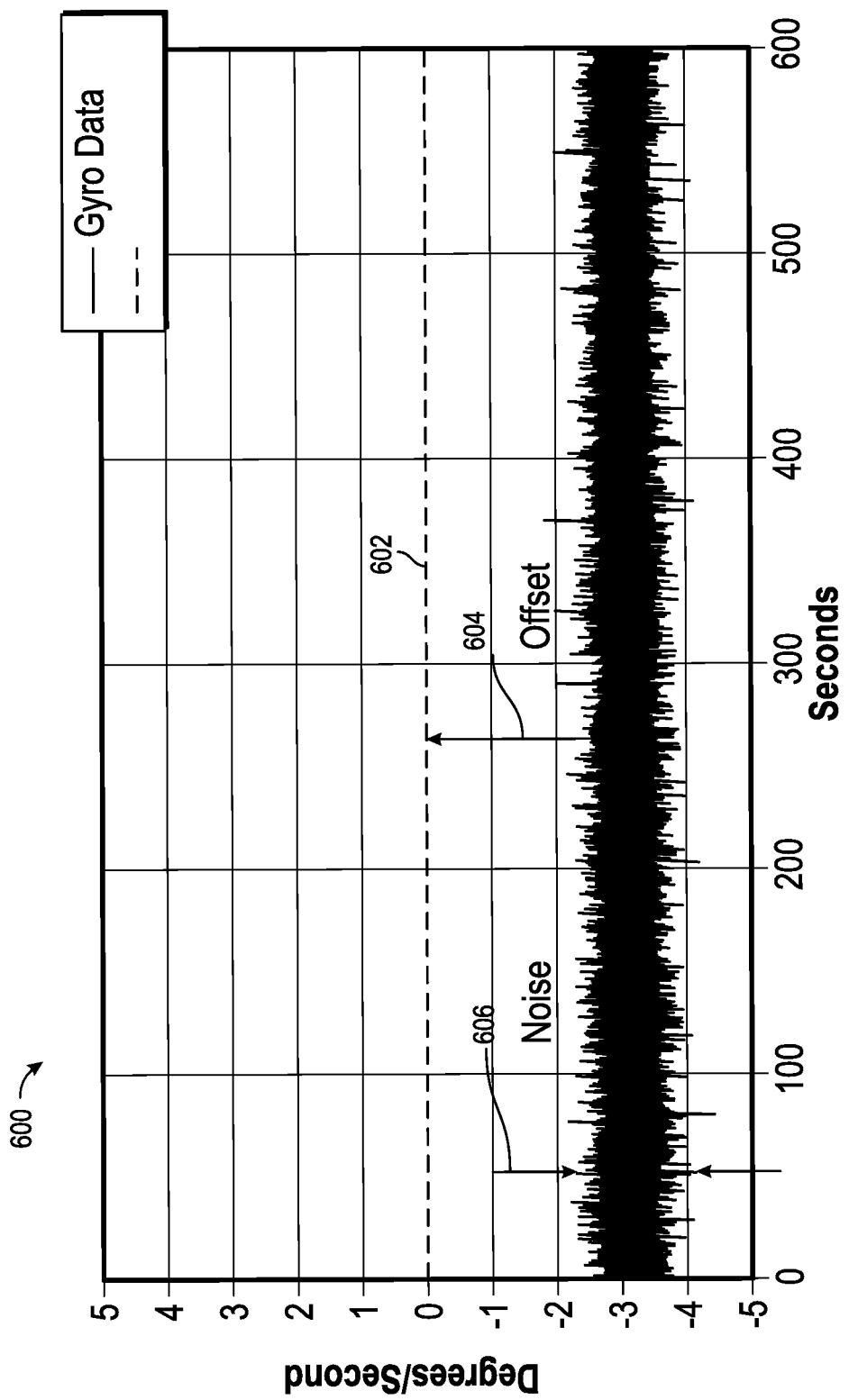
FIG. 6 illustrates gyroscope's uncorrected errors, gyroscope noise, which causes diffusion errors in orientation, and gyroscope offset, which causes drift errors in orientation.

FIG. 6 illustrates gyroscope's uncorrected errors, noise which causes diffusion in sensor's orientation and offset which causes drift in sensor's orientation, at initial power up in an at rest condition. Typically, off-the-shelf accelerometers 112 suffer from offset and scale errors. These errors are reduced via the one-time factory calibration parameters 126; the user need not be concerned about these errors. A three axis gyroscope 114 may measure the three components (X', Y', and Z' in local frame) of an angular velocity ω of the IMU 110. Several factors given below need to be considered to handle data coming from the gyroscope 114:

(i) Noise which causes diffusion in sensor's orientation, 606 (see FIG. 6): Off-the-shelf gyroscopes suffer from noise which causes diffusion in sensor's orientation. As shown in FIG. 6, gyroscope 114 may exhibit a noise magnitude of around ±0.5 degrees/second. The effect of this noise 606 needs to be corrected in the calibration parameter 126. Otherwise, the calculated sensor orientation data would diffuse (random walk) away with time from the correct orientation value. The calibration parameter 126 may correct for this diffusive behavior at run time in the fusion algorithm 126, using a frequency dependent parameter named β, as drift and diffusion correction factors.

(ii) Offset, which causes drift in sensor's orientation, error 614 (see FIG. 6): Gyroscope 114 may also suffer from fixed offset errors in the measured values of angular velocities. As shown, this offset 604 may lead to drift errors in orientation, errors which increase with time linearly. The gyroscope 114 should ideally measure the angular velocity components to be zero. However, the measured results of IMU 110 may show a constant offset error of −3 degrees.

The error readings of noise which causes diffusion in sensor's orientation 606 and offset which causes drift in sensor's orientation, is individually measured at the factory which is specific to each IMU, which may be stored as calibrate parameter 126 in a persistent memory of the MCU to correct the orientation data to exhibit close to zero noise and close to zero offset as shown in line 604 over a time period.

Figure 7:
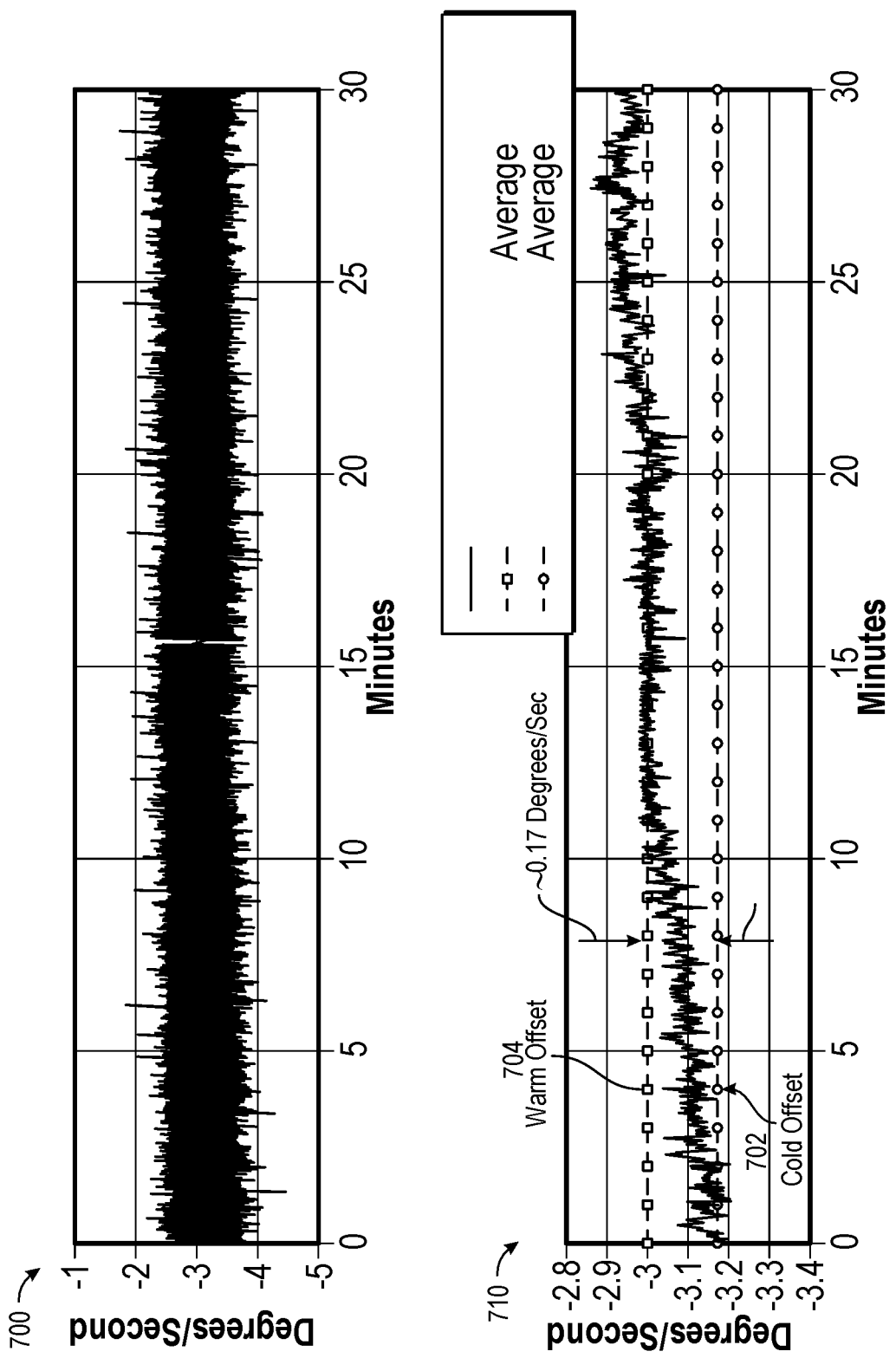
FIG. 7 illustrates gyroscope's uncorrected errors as shown in FIG. 6, during a warm up period in an at rest condition.

FIG. 7 illustrates gyroscope's uncorrected errors as shown in FIG. 6, during a warm up period in an at rest condition. The gyroscope (114) may need a warm up time of the order of 10 to 15 minutes before its cold offset value 702 settles to a warm offset value 704 to steady state values. Typically, it may be difficult to see this warmup behavior since it is often masked by noise. Therefore, some filtering of the data is required to observe this effect. Note how the noise is masking the warmup behavior in the top graph 700 in FIG. 7, and how the warmup is revealed in the bottom graph 710 (where a two second averaging filter is applied to the data) which clearly shows the initial warm-up time 702, before the results settled down to value 704. As discussed later, this type of warmup behavior dictates that the factory calibration for offset should be done after warmup and not when the gyroscope 114 is cold, otherwise significant offset error could occur in gyro data after warmup times, which would lead to appreciable drift. FIG. 7 shows the two different values (701 and 702) of offset that would be obtained if the offset were calculated when the sensor was cold (−3.2 degrees in lower circle-dashed line 702) and when the sensor was warmed up for 15 minutes (−3.0 degrees in upper asterisk-dashed line 701).

Examples of Drift and Magnetic Noise: Since drift plays such an important role in evaluating the performance of an orientation sensor, drift is defined and illustrated with some real-world examples obtained from the sensors. Drift calibration may be achieved in a fusion algorithm 124. Drift may be caused by the offset error in the gyroscope (if appropriate calibration procedures are not followed).

Figure 8A:
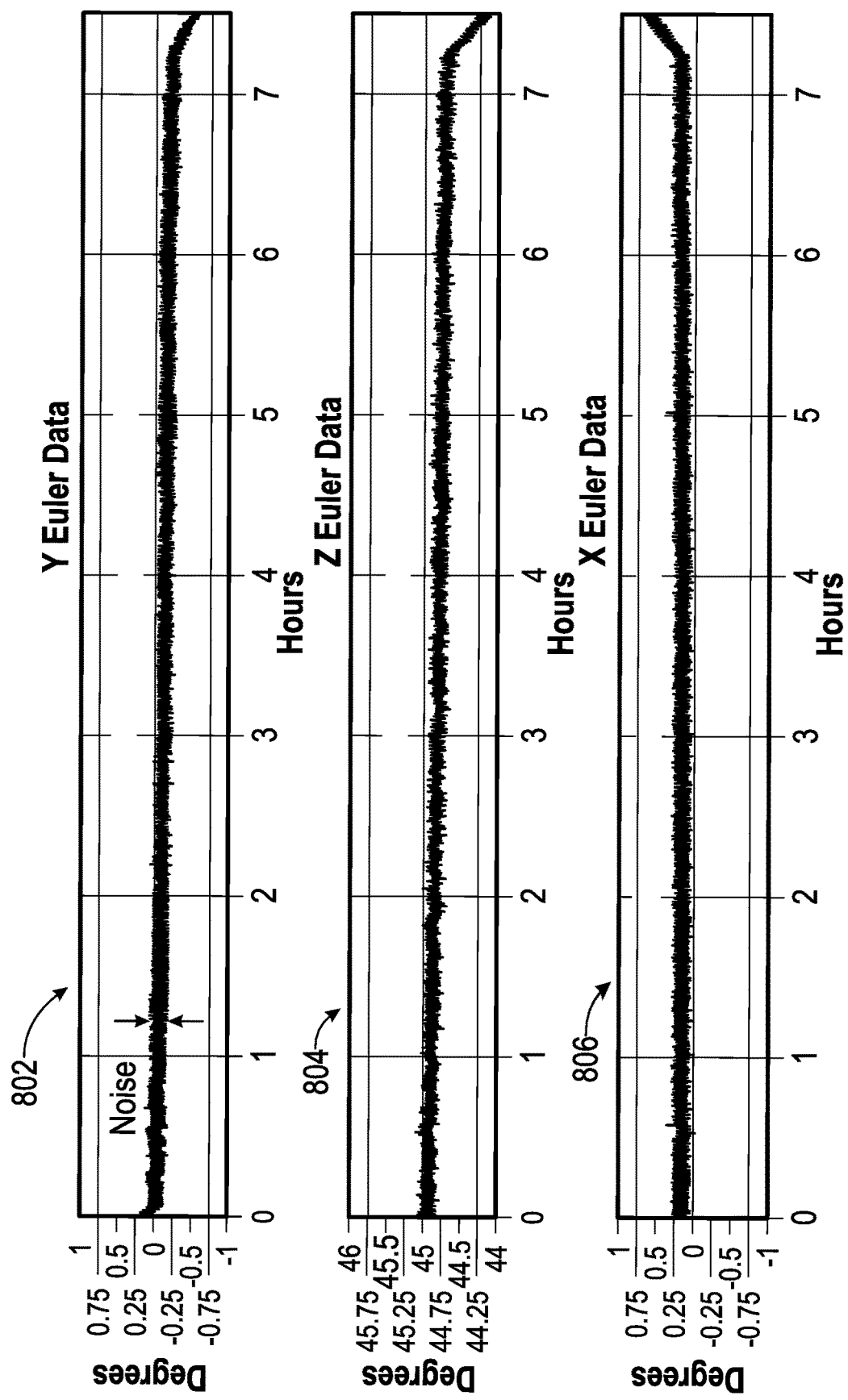
FIG. 8A illustrates orientation Euler angles generated by a sensor over a battery life, in an at rest condition.

FIG. 8A illustrates Euler angles $\theta_x$, $\theta_y$, and $\theta_z$ obtained from the sensor's orientation quaternion q over a battery life, in an at rest condition. The sensor 102 is fastened to a fixed position at least two feet away from any ferromagnetic and magnetic materials. The drift test was started after a 15-minute warmup and the orientation quaternions being periodically read and having corrected with the calibration firmware 126 stored in the persistent memory. As shown in graphs 802, 804 and 806 of FIG. 8A, the calculated Euler angles $\theta_x$, $\theta_y$, and $\theta_z$ remained constant except for noise fluctuations after over 7.5 hours of continuous operations until the battery starts to deplete. It is shown that a total drift of less than 0.25 degrees in all the three Euler angles $\theta_x$, $\theta_y$, and $\theta_z$, this translates to less than 0.035 degrees/hour of drift.

Figure 8B:
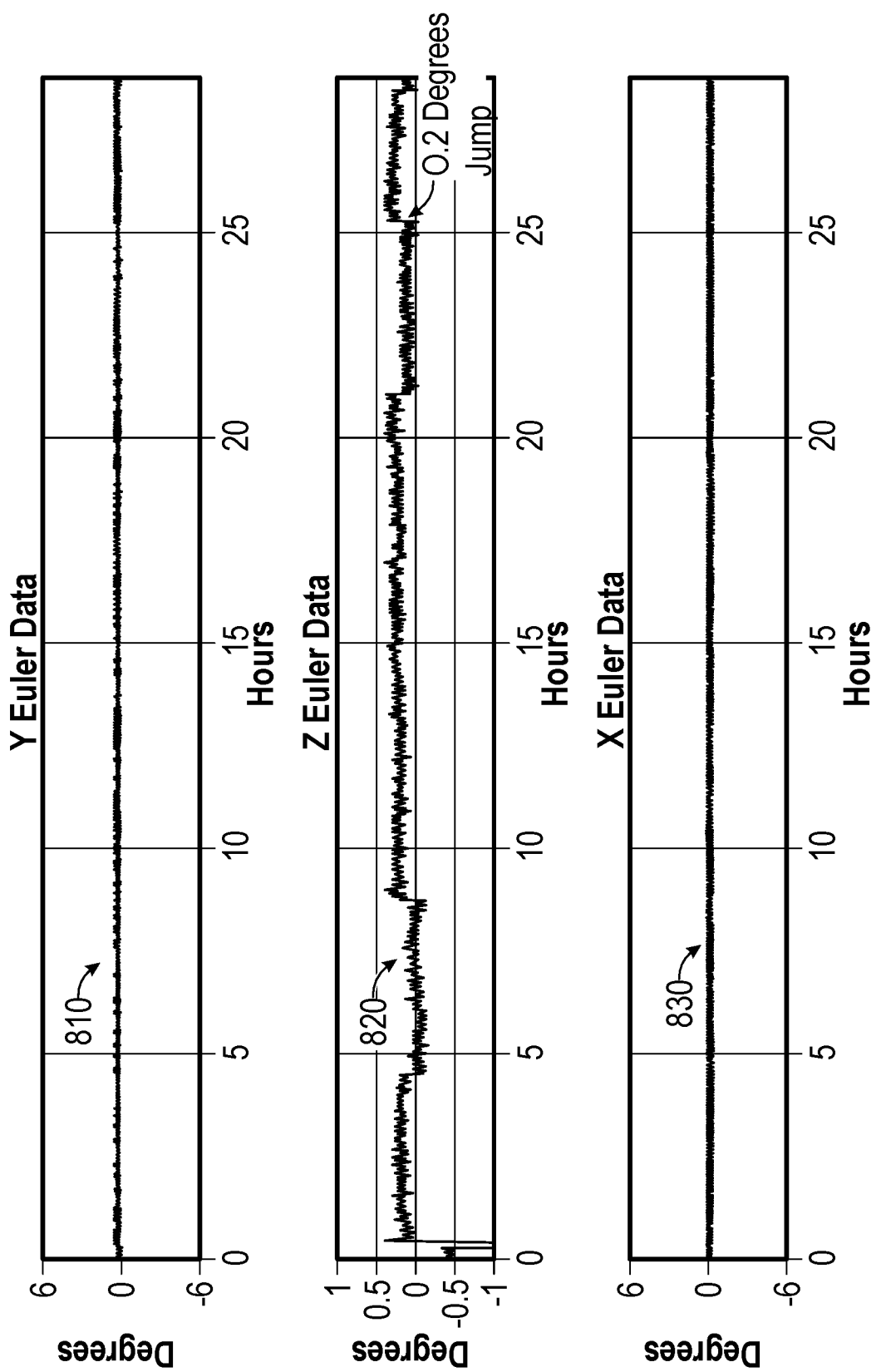
FIG. 8B illustrates magnetometer's distortion in orientation Euler angles caused by magnetic noise during a warm up period in an at rest condition.

FIG. 8B illustrates Euler angles $\theta_x$, $\theta_y$, and $\theta_z$ obtained from the sensor's orientation quaternion in the presence of ferromagnetic interference to demonstrate magnetometer's distortion caused by magnetic noise after a warm up period, in an at rest condition. Graphs 810 and 830 shows an improvement in magnetic noise in y Euler data and x Euler data after compensation. Graph 820 exhibits jumps in z Euler data due to magnetic noise caused by the presence of or within two feet of a ferromagnetic material. Thus, the magnetometer's 116 in the sensor 102 should be kept away from ferromagnetic and magnetic materials at a predefined minimum distance of at least two feet.

Figure 9:
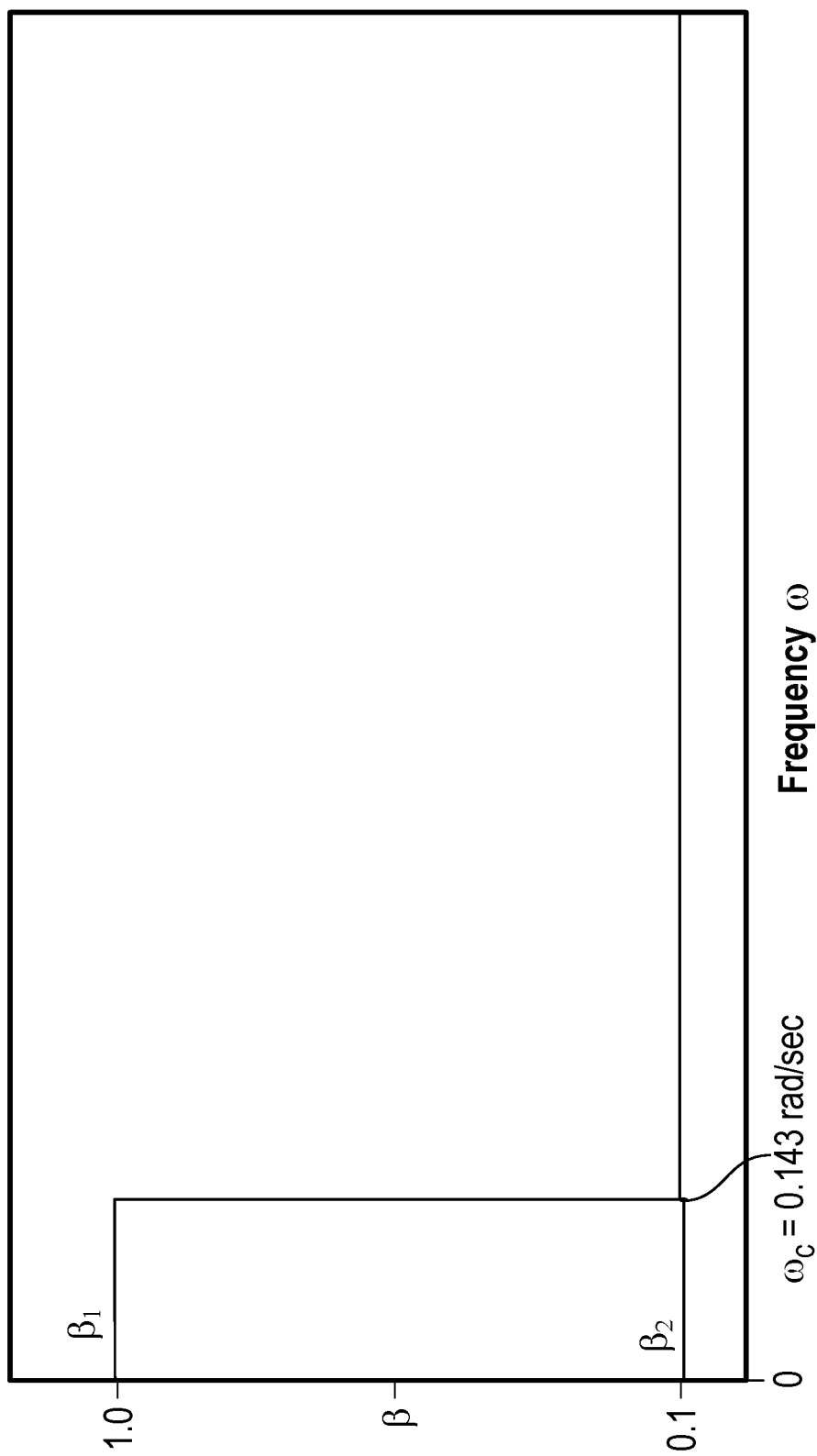
FIG. 9 illustrates a frequency dependent beta R used in a fusion algorithm to improve responsive (less sluggish) transition of the sensor from the sensor's dynamic state to the sensor's semi-static and to improve sensor drift characteristics in semi-static state.

FIG. 9 illustrates using a frequency dependent beta β for drift and diffusion corrections to calibrate a sensor 102 under semi-static state and dynamic state. In an example, the frequency dependent β may include using either a $\beta_1$ or a $\beta_2$ depending on whether or not a sensor's angular frequency ω is greater than a cross-over angular frequency $\omega_c$ as shown in FIG. 9, wherein $\beta_1 > \beta_2$. More specifically, when sensor's $\omega<\omega_c$ in a semi-static state (i.e., stationary to slow motion), $\beta_1$ may be used to compensate for gyroscope drift and diffusion contributions. In the semi-static state, the sensor 102 (having the magnetometer 116) should be kept at a predefined minimum distance away from ferromagnetic and magnetic materials. When sensor's $\omega>\omega_c$ in a dynamic motion state, $\beta_2$ may be used to compensate both magnetometer noise and accelerometer noise contribution in the sensor 102.

The use of at least two βs in a frequency dependent sensor's motion condition is to make the sensor 102 "snappier." In an example, $\beta_1 \geq 1$ for low frequencies ($\omega<\omega_c$) and $\beta_2=0.1$ for higher frequencies ($\omega>\omega_c$), where $\omega_c=0.143$ rad/sec for the cross over frequency. The reason for this approach can be summarized as follows: (a) in a case when $\omega<\omega_c$ which may be a semi-static condition, accelerometer noise should be negligible, therefore a larger value of β (e.g., β1=1) can better take care of the gyro divergent errors (diffusion and drift). However, for larger values of β, the sensor 102 would need to be kept at a predefined distance (e.g., at least two feet away) away from magnetic and ferromagnetic materials to avoid magnetic noise. To keep magnetic noise low, β should remain less than or equal to 1; (b) in a case when $\omega>\omega_c$ which may be a dynamic state condition, a smaller β (e.g., $\beta_2=0.1$) may be used to avoid the higher frequencies accelerometer noise and overall noise in orientation problems.

The smaller β may make the sensor motion appear smooth as they are in motion. The smoothness may be because of less accelerometer noise, and because of less overall noise in the orientation data. However, if the sensor 102 is moved too vigorously, then the orientation quaternion might move away from a minimum of the objective function where the correct solution for the orientation may be when the orientation quaternion is at a minimum of an objective function $f$ to be explained later. In a case of using a single-β solution instead of the proposed at least a two-β solution, if the sensor 102 stops moving, then the small single value of β would take a longer time to reach the minimum due to sluggishness of the sensor 102. Therefore, if using the two-β scheme, as soon as the sensor 102 stops moving, the sensor's β region would transition from a smaller β ($\beta_2=0.1$) to a larger β (β1=1) and the sensor's orientation would quickly snap back to the right answer at the minimum of the objective function. Therefore, using the two-β scheme makes the sensor 102 be more responsive and more agile in orientation calculation, making the orientation readings snappier and smoother to deal with the exceptional semi static correction of gyro divergent errors due to diffusion and drift. Note that the same two β values may be used for all the sensors 102, and the two β values in the calibration parameters are not unique or specific to a given sensor.

Figure 10:
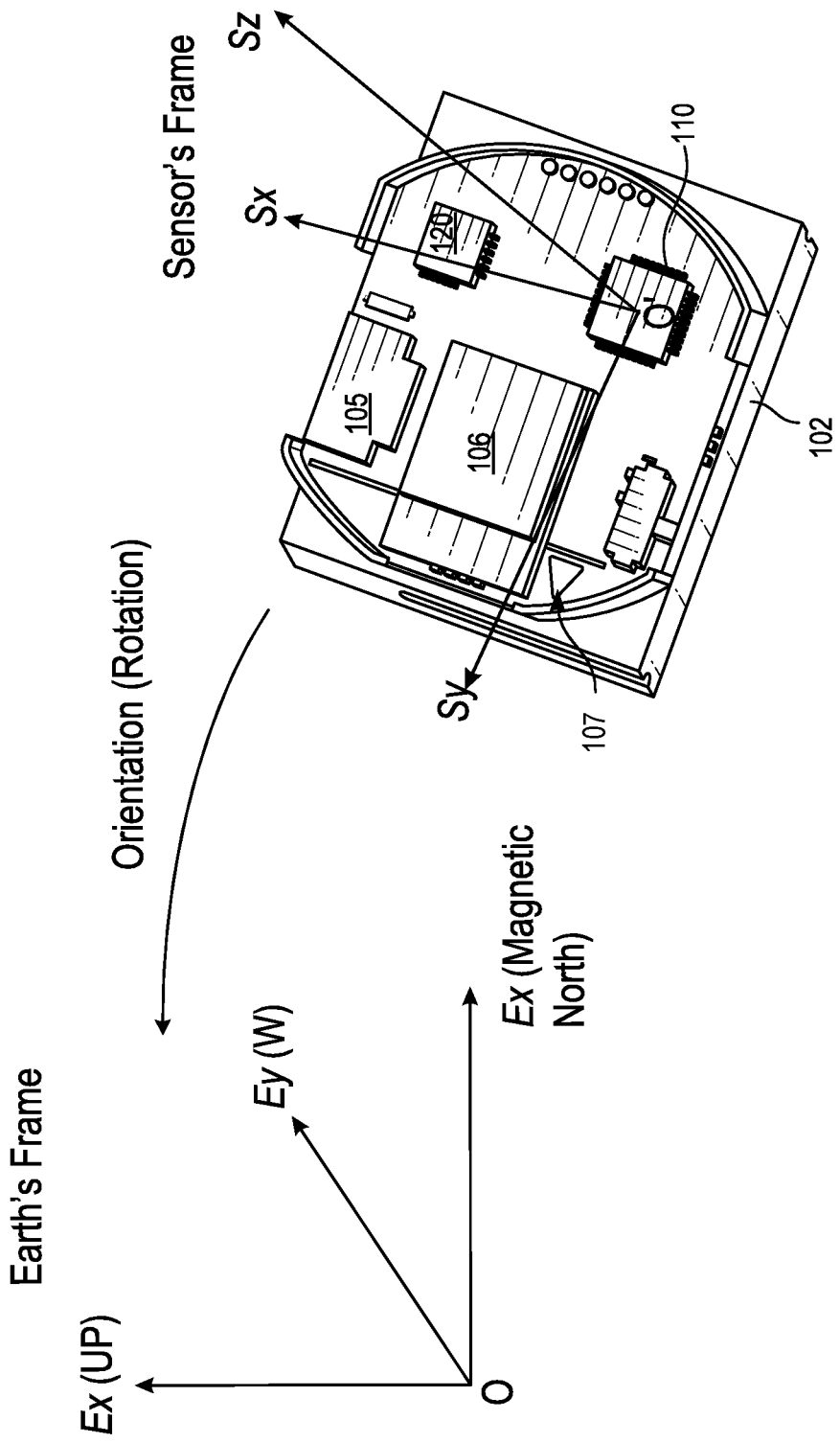
FIG. 10 is an example mapping of a sensor's local frame to a World frame.
Figure 11:
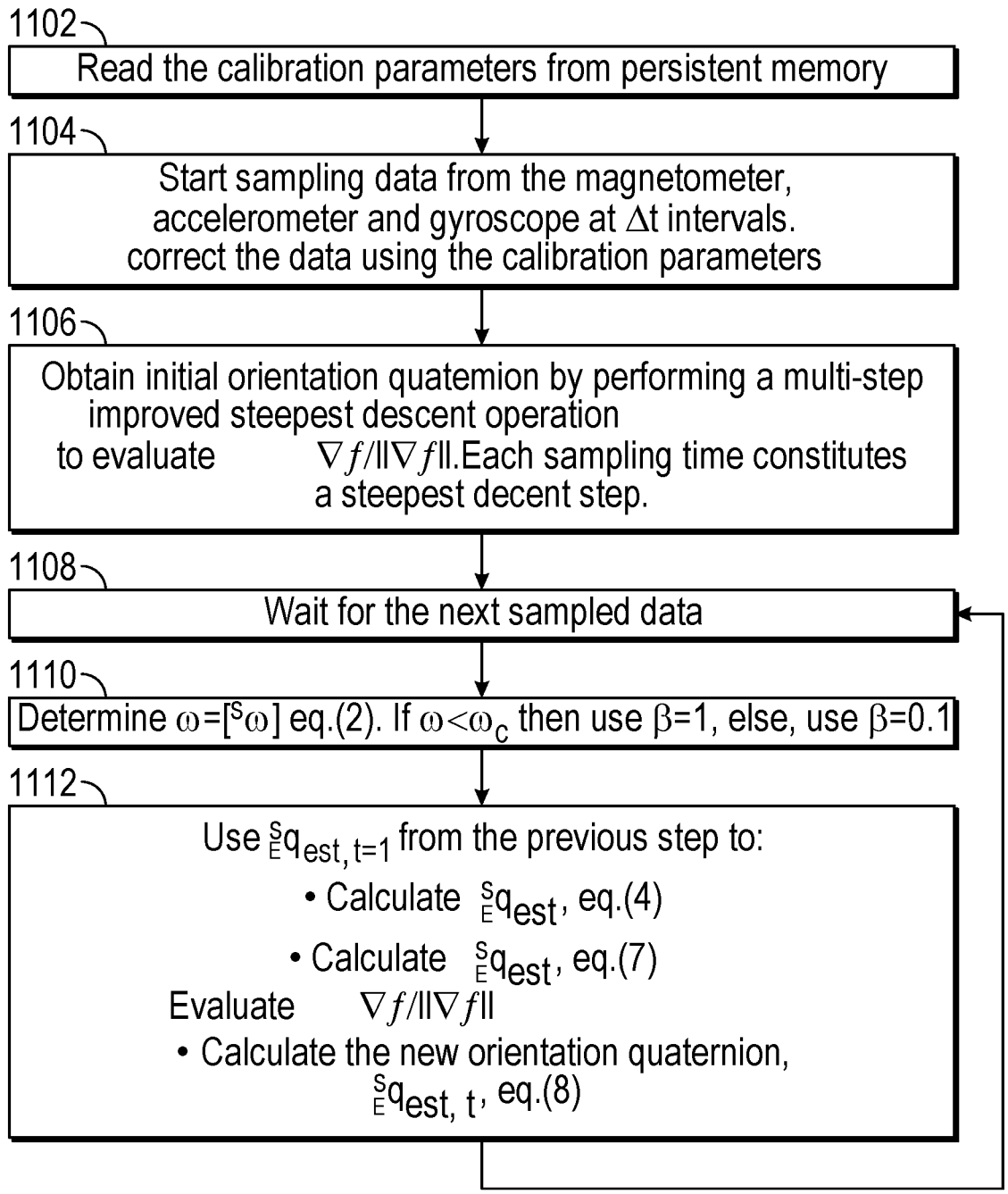
FIG. 11 is an example fusion algorithm flow chart for a sensor orientation measurement.

FIG. 10 is an example mapping of the sensor's frame (local frame) to a World frame. FIG. 11 is an example fusion algorithm flow chart to measure orientation in a sensor 102. The MCU 120 of the sensor 102 may modify Madgwick's fusion algorithm using a frequency dependent β to calculate the orientation quaternion in fixed point. For the sake of convenience, Madgwick's terminology and symbols may be adopted to shown the orientation calculations. A World Frame with the letter E (Earth) and a Sensor's local frame by the symbol S may be adopted.

The Earth's Frame is fixed to the earth and has coordinates, $^Ex, ^Ey, ^Ez$. The orientation of the sensor 102 is defined as the quaternion $_E^S\hat{q}$ which is a rotation that aligns the Sensor's frame with the Earth's frame.

$$_E^S\hat{q}=[q_1,q_2,q_3,q_4] \quad (1)$$

The hat ^ symbol is used to denote a unit quaternion. The job of the fusion algorithm is to periodically calculate the orientation, $_E^S\hat{q}$, after each time step, Δt. The value of Δt is dictated by a sampling rate at which raw data can be read from the IMU's sensors (accelerometer 112, gyroscope 114, and magnetometer 116). The orientation, $_E^S\hat{q}$, can be calculated in two alternate ways: (i) by using the gyroscope 114 raw data alone, or, (ii) by using the raw data obtained from the magnetometer 116, accelerometer 112 (M, A) pair.

As described in prior FIGS. 8-9, using the gyroscope alone may lead to diffusion and drift errors, while using the (M, A) pair by itself will make the sensor 102 sensitive to accelerometer and magnetic noise. In this example, the orientation, $_E^S\hat{q}$ calculation may be obtained from steps (i) or (ii) by modifying Madgwick's fusion algorithm using a frequency dependent β value, which can be summarized by the flow chart of FIG. 11 as follows:

Step 1102: starting from a fully calibrated sensor by reading the calibration parameters 126 from persistent memory. Steps 1104-1106: calculate the initial orientation using the (M, A) pair, then perform the following operations periodically after each time step (or time interval) Δt. Start sampling raw data from the magnetometer 116, accelerometer 112 and gyroscope 114 at each time interval Δt, correct the raw data using the calibration parameters. Step 1106: calculate the change in orientation by using the gyroscope raw data only. Step 1108, wait for the next sampled raw data within the time interval Δt. The above steps 1106-1108 will lead to small diffusion errors (explained earlier) in orientation due to gyro noise, and some drift due to gyro offset even in a calibrated gyroscope 114.

Step 1110-1112: correct the orientation for these gyro errors by calculating the change in orientation by using the (M, A) pair. The amount of this (M, A) change is weighted by at least two parameters, βs (explained earlier). For typical sensors, the errors introduced by using the gyroscope 114 raw data alone from step (i) are small in the time step, Δt, so a small value of β<1 may be enough to correct for the gyro errors. Keeping the value of β small has the advantage of reducing the dependence of orientation on accelerometer and magnetic noise. The weighing parameters, (for example, $\beta_1=1.0, \beta_2=0.1$) may be determined empirically to be the best noise and accuracy in the calculated orientation. Go to steps 1108-1112, and continue indefinitely to correct gyro errors.

The operations of steps 1108-1112 may be explained in more detail in the following sections. In practice, the sequence of carrying out the steps may be to first look at orientation calculated from gyro data (i), and then carry out the calculations using the (M, A) pair (ii), followed by fusing the two results from steps (i) and (ii) using one of the two values of β ($\beta_1=1.0$) and ($\beta_2=0.1$).

Regarding step 1108 in the orientation calculation from gyroscope data: a gyroscope 114 generates three components of the angular velocity, $\omega_x, \omega_y,$ and $\omega_z$. The corresponding angular acceleration quaternion, $^S\omega$, may be generated as blow equation (2):

$$^S\omega=[0,\omega_x,\omega_y,\omega_z] \quad (2)$$

from which a rate of change of orientation can be obtained with respect to time (⊗ indicates quaternion multiplication) as shown in equation (3).

$$_E^S\dot{q}_{\omega,t} = \frac{1}{2}{}_E^S\hat{q}_{\omega,t} \otimes {}^S\omega_t \quad (3)$$

The subscript ω indicates that (in this section) the orientation may be obtained from gyro data only, and the subscript t indicates time. To evaluate the orientation, $_E^S q_{\omega,t}$, from $_E^S \dot{q}_{\omega,t}$ it is necessary to numerically integrate this equation (3) with respect to (w.r.t) time t. To accomplish the integration, $^S \omega_t$ is sampled periodically at times t, t+Δt, t+2Δt, ... (henceforth, t, t+1, t+2, ... as short-hand for t, t+Δt, t+2Δt, ...). The integration is performed by estimating the orientation, $_E^S q_{est,\omega,t}$, at time t by using the previously estimated value of the orientation, $\hat{q}_{est,\omega,t-1}$, at time t−1. With the passage of time, new terms are added to older terms and a sequence of sums is built up to perform the integration numerically through equations (4)-(5):

$$_E^S \dot{q}_{\omega,t} = \frac{1}{2} {}_E^S \hat{q}_{est,t-1} \otimes {}^S \omega_t \qquad (4)$$

$$_E^S q_{est,\omega,t} = {}_E^S \hat{q}_{est,t-1} + {}_E^S \dot{q}_{\omega,t} \Delta t \qquad (5)$$

Note that an initial value of the orientation, $\hat{q}_{est,t=0}$, is to get an iterative sum started. However, the gyroscope has no way of determining this initial orientation since it can only give changes in the orientation with respect to time. The (M, A) pair is used to determine the initial orientation to get the above integration started. How the (M, A) pair calculates orientation will be explained.

If the gyroscope data had no noise or offset errors, then the above integration algorithm is all that would be required to get accurate sensor's orientation (provided the time interval, Δt, is chosen appropriately small). However, the presence of noise and offset in the gyroscope data cause errors in the orientation, $_E^S q_{\omega,t}$, in the form of diffusion and drift.

Diffusion errors: For simplicity, assume that the gyroscope data has noise but no offset. If the sensor is at rest (i.e., semi-static or static state), then ideally the orientation will not change with time since $^S \omega_t$ would be zero at all times. However, noise in the gyroscope will make the orientation move randomly and diverge away from the initial position in a random manner. This random motion is like diffusion (or random walk) present in many physical phenomena.

Similarly, noise in the gyroscope may cause the orientation of the gyroscope 114 to diffuse and diverge away from its starting value, even if the gyroscope 114 is at rest. Therefore, gyro noise will cause the orientation to diverge away from the true orientation of the sensor. The larger the value of the gyro noise, the larger will be the extent of diffusion. The (M, A) pair and an appropriate value of β will be used in the fusion algorithm to correct for diffusion which is caused by noise in the gyroscope 114. Note that the gyroscope 114 does not know the true orientation, it only knows the change of orientation with respect to time; therefore a gyroscope 114 has no way of correcting for diffusion on its own, it needs the help of the (M, A) pair to correct for diffusion. Diffusion (caused by noise in the gyroscope 114) is also known as divergent because it takes the orientation of the sensor 102 away from the correct value.

Drift error: If the gyroscope data has a constant offset error then the integration discussed above results in an error in orientation, $_E^S q_{\omega,t}$, which increases linearly with time. This error is known as drift. As a one-dimensional example, integration over an offset error of constant, c, would lead to ct, a term linear in time, t, related by equation (6):

$$\int_0^t c\, dt = ct. \qquad (6)$$

This drift error may be corrected by calibrating the gyroscope to remove the offset from the orientation data as described above. If the drift is small, then a small value of β can be used to handle it. In general, using large values of β to remove drift are best avoided since that makes the orientation more susceptible to accelerometer and magnetometer noise. Note that even though the sensor is motionless (semi-static or static state), the calculated orientation is increasing linearly with time. Drift makes stationary objects appear to rotate at a constant angular velocity, equal to a slope of a drift line.

Orientation calculation from the (M, A) Pair Data: In this section it will be described how the data from the magnetometer and accelerometer pair can alternately be used to calculate the orientation. Madgwick's paper provided that the rate of change of orientation with respect to time, $_E^S \dot{q}_{\epsilon,t}$, be expressed as equation (7) below:

$$_E^S \dot{q}_{\epsilon,t} = \frac{\nabla f}{\|\nabla f\|} \qquad (7)$$

Here, ε indicates that data from the (M, A) pair was used to determine the rate of change of orientation. f is a function of the orientation quaternion, $_E^S q_{\epsilon,t}$, known as the objective function, ∇f is the gradient of f, and ‖∇f‖ denotes the magnitude (length) of ∇f. The objective function f is a fairly complicated function explained fully in Madgwick's paper, where it is shown that minimizing this function with respect to $_E^S q_{\epsilon,t}$ determines the orientation of the sensor. Since ∇ is the gradient operator, ∇f/‖∇f‖ points in the direction of the minimum, and becomes zero at the minimum, at which point $_E^S q_{\epsilon,t}$ becomes the correct value of the orientation. So, determining the value of the orientation can be reduced to the problem of optimizing f (i.e. finding its minimum), which can be done by using ∇f/‖∇f‖ in conjunction with the steepest descent method.

Recall that ∇f has a direction which points in the direction of the minimum of the objective function. Because orientation is being calculated by using two sensors, (M, A) pair, ∇f is composed of two directions. One direction is caused by changes in magnetometer data, and the other caused by changes in accelerometer data. To reach the minimum of f in the most optimal way, these two directions should be close to being orthogonal to each other, so that the minimum can be found (by the steepest descent method) in the least number of steps.

It turns out that in Madgwick's original paper, the way ∇f is defined, these two directions are not orthogonal, which can lead to slow dynamic response, i.e., the system can take some time to reach the minimum of f. Madgwick's non-orthogonal method is called the "original" steepest descent method.

An improvement is made in to Madgwick's steepest descent method by using orthogonal directions. More specifically, the magnetic and accelerometer directions of ∇f are orthogonal to each other. This can lead to significant improvement in reducing the number of steps required to reach the minimum, therefore leading to better dynamic response. This method is called the "improved" steepest descent method.

In practice, a full steepest descent minimization using the (M, A) pair is performed only at the beginning of the algorithm, to set the right initial conditions for the integrations in the algorithm. After this step, one could simply (numerically) integrate $_E^S \dot{q}_{\epsilon,t}$ using the equation given above, and determine the orientation at the sampling times t, t+1, t+2 . . . . However these results would be overly susceptible to magnetic and accelerometer noise. Instead, as described in the next section, the fused orientation results may be obtained from the gyroscope 114 with those obtained from the (M, A) pair.

The modification to the fusion algorithm includes fusing gyroscope and (M, A) Pair Data by using a frequency dependent value of β. The fusion of the gyro and (M, A) data is obtained by combining the rate of change of orientation obtained from the gyroscope, $_E^S\dot{q}_{\omega,t}$, eq. (4), with the rate of change of orientation obtained from the (M, A) pair, $_E^S\dot{q}_{\epsilon,t}$, eq. (7) as follows:

$$_E^S q_{est,t} = _E^S \hat{q}_{est,t-1} + (_E^S \dot{q}_{\omega,t} - \beta _E^S \dot{q}_{\epsilon,t}) \Delta t \qquad (8)$$

This equation (8) is a numerical integration performed in the main loop of the fusion algorithm. The frequency dependent β is an adjustable parameter which glues the two results, i.e., gyroscope's orientation data and orientation obtained from the (M, A) pair together. When β=0 pure gyro results are obtained, eq. (5), and when β is very large ($\beta_1$=1.0) then the second term in brackets of eq. (8) becomes the larger term and the (M, A) pair term dominates; eq. (8) reduces to a numerical integration of eq. (7).

It will be shown in FIG. 11, that starting from a fully calibrated sensor 102 the fusion algorithm may calculate the initial condition (see steps 1102, 1104 in FIG. 11) for the integration in eq. (8) by using the multiple step steepest descent method (using M, A pair data), until convergence is obtained. Then periodically calculate the change in orientation by using (8). The integration of the term $_E^S\dot{q}_{\omega,t}$ Δt in eq (8) will lead to diffusion errors due to gyro noise, and may also contain a small amount of drift due to gyro offset, even in a calibrated gyroscope (gyro calibration is discussed later); where both of these errors are divergent as explained earlier. The term $\beta _E^S\dot{q}_{\epsilon,t}$ Δt in eq. (8) is convergent, i.e., it adjusts the orientation in the correct direction, since it is proportional to $\nabla f / \|\nabla f\|$, eq. (7), and is directed towards the minimum of the objective function $f$ i.e., the correct orientation.

Note that the frequency dependent β directly controls the size of the convergent correction. Keeping β small ($\beta_2$=0.1) has the advantage of reducing the dependence of orientation on accelerometer and magnetic noise. On the other hand, keeping β large has the advantage of correcting the divergent errors better.

A large value of β ($\beta_1$>1.0) also has the disadvantage of increasing the noise in the calculated orientation. This can be explained as follows: After the initial full steepest descent calculation, the system comes to the minimum of the objective function. For the rest of the integration loop, the answer remains near this minimum. The divergent terms derive the system away from the minimum, while the convergent terms bring it in the direction of the minimum. However, the convergent team is scaled by β, and depending on the value of β the system will overshoot the minimum by some amount. Thus, the calculated orientation will "rattle around" the minimum with the passage of time. This "rattling around" because of overshoot will appear as noise in the calculated orientation data. Therefore, larger values of β lead to an increased noise in orientation.

It is shown through the above described methods and systems that the IMU 102 (e.g., 9-axis inertial modules by ST Microelectronics of Geneva, Switzerland) can achieve high performance with almost zero drift over its useful battery life find applications in those that are typically only seen with higher grade IMUs.

The improvement in drift performance on low grade IMUs can be achieved through performing in the following sequence as shown in FIG. 11: warming up the IMU 102, calibrating the gyroscope raw data using factory pre-installed IMU specific calibration data, afterwards executing a fast converging fusion algorithm to calculate orientation information from the raw data sampled from the IMU 110. It is shown that Madgwick's fusion algorithm which is used to calculate orientation in quaternions from the corrected raw data of the IMU, may be improved to respond with more agility and to converge the orientation information faster to minimum drift errors. More specifically, the improved fusion algorithm uses a frequency dependent β to glue the gyroscope's calibrated raw data and the (M, A) pair calibrated raw data together in orthogonal directions to perform a steepest descent method to a fast convergence to a minimum solution.

Furthermore, it is shown that the disclosed sensor 102 is able to achieve a long battery life through the use of an ultra-low power MCU 120 (e.g., MSP430 microcontroller by Texas Instruments of Dallas, Tex., U.S.A.) by carrying out fixed point calculations on the fast convergence fusion algorithm.

The sensor 102 formed by a pair lower grade IMU 110 and ultra-low power MCU 120 sensor find many high-valued applications such as knee arthroplasty, prosthesis apparatuses, robotics, computer-guided surgical procedure, posture corrections in rehabilitation and physical therapy, in augmented reality or possibly remote spacewalk repairs, which opens to an unlimited larger "total addressable market".

Other systems, methods, features, and advantages will be, or will become, apparent to one with skill in the art upon examination of the figures and detailed description. It is intended that all such additional systems, methods, features, and advantages be included within this description, be within the scope of the disclosure, and be protected by the following claims.

What is claimed is:

1. A method for measuring orientations in a sensor, the method comprising:
    sampling within a periodic time interval Δt by an inertial measurement unit (IMU), a plurality of IMU data samples generated by a magnetometer, an accelerometer, and a gyroscope comprised in the IMU, wherein each IMU data sample is oriented according to a local frame in the IMU;
    sending the plurality of IMU data samples to a microcontroller unit (MCU) to generate a corresponding plurality of sensor's orientation data samples through operations, comprising:
        reading from an on-board persistent memory, calibration parameters to correct each of the plurality of IMU data samples to stay within a pre-defined range of orientation accuracy and/or drift variations;
        executing an on-board fusion algorithm in a fixed point to rotate by an amount, to align the local frame of each corrected plurality of IMU data samples to match a world frame, and to transform the corrected plurality of IMU data samples to the corresponding plurality of sensor's orientation data samples; and
        transmitting the corresponding plurality of sensor's orientation data samples to a remote station; and
    using two drift and diffusion correction factors $\beta_1$ and $\beta_2$ in the calibration parameters, wherein $\beta_1 > \beta_2$ and $\beta_1$ is used to compensate for gyroscope drift and diffusion contributions in a semi-static state where the IMU is to be kept away from ferromagnetic and magnetic materials at a predefined minimum distance, and where a measured angular frequency ω is less than or equal to a cross-over angular frequency $\omega_c$, and $\beta_2$ is used to compensate for both magnetometer noise and accelerometer noise contribution in a dynamic motion state where the measured angular frequency ω is greater than the cross over angular frequency $\omega_c$.

2. The method according to claim 1, wherein the local frame in the IMU forms a right handed X', Y', and Z' coordinate system with respect to a common origin O', and directions of X' and Y' axes are pre-oriented on the IMU, and wherein the world frame forms a right-handed X, Y, and Z coordinate system with respect to a common origin O, with an x-axis that points in a magnetic North direction, a z-axis that points upward with respect to the earth ground, and a y-axis that is perpendicular to an XZ plane.

3. The method according to claim 1, wherein the magnetometer is a 3-axis magnetometer that measures the X', Y', and Z' coordinates according to a magnetic field's direction vector (North pole) of the IMU in the local frame, wherein the accelerometer is a 3-axis accelerometer that measures the X', Y', and Z' coordinates according to an acceleration of the IMU in the local frame, and wherein the gyroscope is a 3-axis gyroscope that measures the X', Y', and Z' coordinates of an angular velocity of the IMU in the local frame.

4. The method according to claim 1, wherein the calibration parameters are IMU specific, are determined at factory and stored in a persistent memory as firmware to be read by the MCU to correct the IMU data samples generated by the magnetometer, the accelerometer, and the gyroscope, prior to the alignment of the local frame to the world frame.

5. The method according to claim 1, wherein the rotation of the local frame to align with the world frame are calculated in quaternions, and the corresponding plurality of sensor's orientation data samples are transmitted as quaternions to avoid gimbal lock.

6. The method according to claim 1, wherein the sensor is an integrated package device to include at least the IMU, the MCU, the persistent memory, a transceiver, and a battery.

7. The method according to claim 1, wherein orientation accuracy is improved by performing a steepest descent operation to find a minimum of an orientation function f through determining a rate of change of orientation quaternion by comparing a current IMU data sample's orientation quaternion at time t with a previous IMU data sample's orientation quaternion at time t−1 in order to determine an amount of rotation required to offset the orientation quaternion to generate the sensor's orientation data sample.

8. The method according to claim 7, wherein the steepest descent operation is iteratively performed on all subsequent IMU data samples' orientation quaternions within the time interval Δt, to generate corresponding subsequent sensor's orientation data samples.

9. The method according to claim 1, wherein IMU's gyroscopic drift correction is offset after a predetermined warm up time.

10. A system for measuring orientations, the system comprises:
an inertial measurement unit (IMU) which samples within a periodic time interval Δt, a plurality of IMU data samples generated by a magnetometer, an accelerometer, and a gyroscope comprised in the IMU, wherein each IMU data sample is oriented according to a local frame in the IMU;
a microcontroller unit (MCU) which receives the plurality of IMU data samples to generate a corresponding plurality of sensor's orientation data samples, wherein:
the MCU reads from an on-board persistent memory, calibration parameters to correct each of the plurality of IMU data samples to stay within a pre-defined range of orientation accuracy and/or drift variations;
the MCU executes an on-board fusion algorithm in a fixed point to rotate by an amount, to align the local frame of each corrected plurality of IMU data samples to match a world frame, and to transform the corrected plurality of IMU data samples to the corresponding plurality of sensor's orientation data samples; and
a transceiver that transmits the corresponding plurality of sensor's orientation data samples to a remote station;
wherein the MCU uses two drift and diffusion correction factors $\beta_1$ and $\beta_2$ in the calibration parameters, wherein $\beta_1 > \beta_2$, and $\beta_1$ is used to compensate for gyroscope drift and diffusion contributions in a semi-static state where the IMU is to be kept away from ferromagnetic and magnetic materials at a predefined minimum distance, and where a measured angular frequency ω is less than or equal to a cross-over angular frequency $\omega_c$, and $\beta_2$ is used to compensate for both magnetometer noise and accelerometer noise contribution in a dynamic motion state where the measured angular frequency ω is greater than the cross over angular frequency $\omega_c$.

11. The system according to claim 10, wherein the local frame in the IMU forms a right handed X', Y', and Z' coordinate system with respect to a common origin O', and directions of X' and Y' axes are pre-oriented on the IMU, and wherein the world frame forms a right-handed X, Y, and Z coordinate system with respect to a common origin O, with an x-axis that points in a magnetic North direction, a z-axis that points upward with respect to the earth ground, and a y-axis that is perpendicular to an XZ plane.

12. The system according to claim 10, wherein the magnetometer is a 3-axis magnetometer that measures the X', Y', and Z' coordinates according to a magnetic field's direction vector (North pole) of the IMU in the local frame, wherein the accelerometer is a 3-axis accelerometer that measures the X', Y', and Z' coordinates according to an acceleration of the IMU in the local frame, and wherein the gyroscope is a 3-axis gyroscope that measures the X', Y', and Z' coordinates of an angular velocity of the IMU in the local frame.

13. The system according to claim 10, wherein the calibration parameters are IMU specific, are determined at factory and stored in a persistent memory as firmware to be read by the MCU to correct the IMU data samples generated by the magnetometer, the accelerometer, and the gyroscope, prior to the alignment of the local frame to the world frame.

14. The system according to claim 10, wherein the rotation of the local frame to align with the world frame are calculated in quaternions, and the corresponding plurality of sensor's orientation data samples are transmitted as quaternions to avoid gimbal lock.

15. The system according to claim 10, wherein the sensor is an integrated package device to include at least the IMU, the MCU, the persistent memory, a transceiver, and a battery.

16. The system according to claim 10, wherein orientation accuracy is improved by performing a steepest descent operation to find a minimum of an orientation function f through determining a rate of change of orientation quaternion by comparing a current IMU data sample's orientation quaternion at time t with a previous IMU data sample's orientation quaternion at time t−1 in order to determine an amount of rotation required to offset the orientation quaternion to generate the sensor's orientation data sample.

17. The system according to claim 16, wherein the steepest descent operation is iteratively performed on all subsequent IMU data samples' orientation quaternions within the time interval Δt, to generate corresponding subsequent sensor's orientation data samples.

18. The system according to claim 10, wherein IMU's gyroscopic drift correction is offset after a predetermined warm up time.

* * * * *